(12) United States Patent
Malov

(10) Patent No.: US 6,688,746 B2
(45) Date of Patent: Feb. 10, 2004

(54) FIELD TESTING USING SPREAD SPECTRUM TECHNIQUE

(76) Inventor: Iouri Malov, 49 Holmes St., Turramurra, New South Wales 2074 (AU)

( * ) Notice: Subject to any disclaimer, the term of this patent is extended or adjusted under 35 U.S.C. 154(b) by 0 days.

(21) Appl. No.: 10/148,650
(22) PCT Filed: Dec. 1, 2000
(86) PCT No.: PCT/AU00/01483

§ 371 (c)(1),
(2), (4) Date: Sep. 23, 2002

(87) PCT Pub. No.: WO01/39659
PCT Pub. Date: Jun. 7, 2001

(65) Prior Publication Data
US 2003/0156255 A1 Aug. 21, 2003

(30) Foreign Application Priority Data

Dec. 3, 1999 (AU) ............................................. PQ 4434
Feb. 11, 2000 (AU) ............................................. PQ 5555

(51) Int. Cl.[7] ................................................ A61B 3/02
(52) U.S. Cl. ...................................... 351/239; 600/558
(58) Field of Search ................................. 351/222, 223, 351/224, 239, 240, 243, 244, 246; 600/558

(56) References Cited

U.S. PATENT DOCUMENTS 4,846,567 A * 7/1989 Sutter .......................... 351/224
6,260,970 B1 * 7/2001 Horn ........................... 351/246
6,315,414 B1 * 11/2001 Maddess et al. ............. 351/246
6,364,845 B1 * 4/2002 Duffy et al. ................. 600/558

FOREIGN PATENT DOCUMENTS

| AU | 3386493 | 9/1993 |
| WO | 8901757 | 3/1989 |
| WO | 9529627 | 11/1995 |

* cited by examiner

Primary Examiner—George Manuel
(74) Attorney, Agent, or Firm—Ladas & Parry

(57) ABSTRACT

There is provided a method of providing a visual reaction map of at least part of the visual field of an eye of a subject, the method comprising: (a) presenting to said visual field a plurality of segments each of the segments comprising an individually activated image; (b) changing each of said individually activated images in each of said segments according to a binary sequence each of said images being changed in a different way from all other of said images whereby the changing of one of said images does not substantially correlate with the changing of any of the other of said images; (c) detecting measurements signals in said subject while said visual field is presented with said changing; (d) correlating said measurement signals with each of the binary sequences used to activate each of said individual segments; and (e) providing said visual reaction map from said correlating. Generally the method further comprises (f) determining from said visual reaction map whether said eye has one or more areas of defective vision.

24 Claims, 14 Drawing Sheets

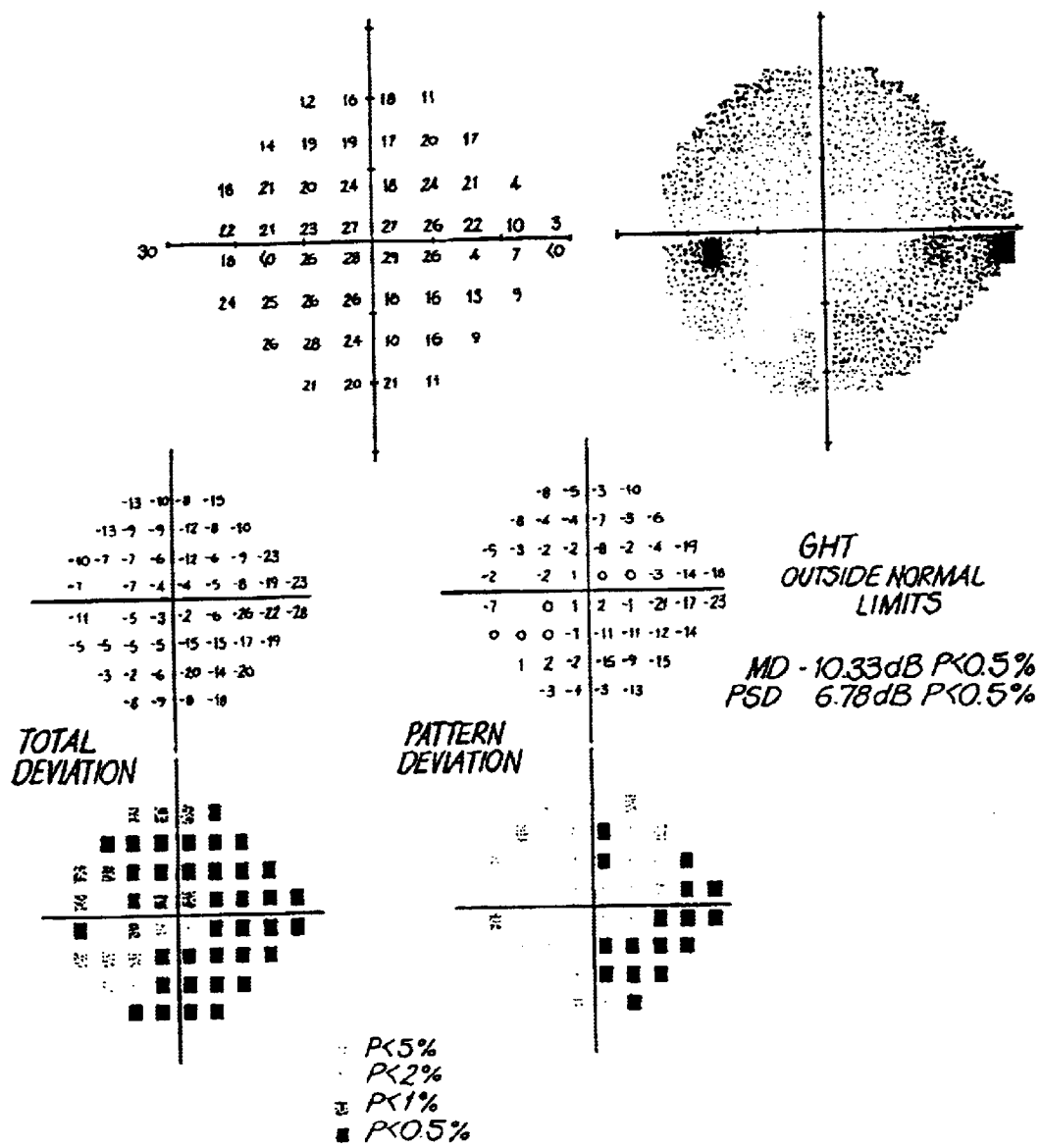
FIG. 7b(ii)

FIELD TESTING USING SPREAD SPECTRUM TECHNIQUE

TECHNICAL FIELD

This invention relates to a method of assessing the integrity of the visual field by objective elecrophysiological recording with simultaneous multifocal stimulation using different stimulus sequences for each part of the field. In particular, it relates to a method for accurately diagnosing and assessing the extent of visual field loss in a glaucoma patient or any other neuro-ophthalmic disorders where there is loss of peripheral vision. It provides for more rapid collection and assessment of data during the recording than any pre-existing technology.

BACKGROUND ART

In determining the extent of damage to the visual system in ocular diseases such as glaucoma, investigation of the visual field (peripheral vision) is vital. Until recently this has relied on subjective psychophysical tests known as perimetry of which the most widely used is the Humphrey visual field analyser. This involves presentation of stimuli of varying luminance in different parts of the visual field to determine visual thresholds and relies on patient decisions. Perimetry therefore involves an element of uncertainty in interpretation of patient responses.

There is a strong demand for an objective measurement of the visual field, to supplement the variable performances seen in perimetry and other psychophysical tests in the evaluation of glaucoma—a disease which is one of the commonest causes of blindness. Recording of the electrical responses generated by the visual system in response to changing stimuli is a possible alternative. Until recently however, electrophysiological recording could only provide a summed response from the whole eye or occipital cortex, and could not assess peripheral vision.

The conventional full field visual evoked potential (VEP) provides information mostly about the central visual field. It is reported to be abnormal in about half of the population with glaucoma. Since many patients can have normal responses, this method gives poor and unreliable discriminatory power for the detection of the disease. The variable findings have previously been explained by the fact that the VEP predominantly reflects macular function and in glaucoma the damage tends to affect central vision late in the disease. With suitable recording conditions and an array of bipolar electrodes positioned overlying the visual cortex of the brain, it was shown [in Graham, Klistorner, Grigg and Billson Invest 1999 Ophthalmol Vis Sci, 40(4) ARVO abstract #318] to be possible to examine the peripheral visual field which is damaged early in glaucoma.

A major advance in stimulus and recording technology has recently been introduced which enables the presentation of a multifocal stimulus. This is now commercially available as the VERIS—Scientific system (Electro-Diagnostic Imaging, Inc., San Francisco) or Retiscan (Roland Instruments, Wiesbaden, Germany). These systems both present a similar method for topographical analysis of recordings, and utilise the orthogonal property of different phases of a special type of binary sequence, called an m-sequence, which allows stimulation of a number of sites of the visual field simultaneously. All elements of the field are stimulated with the same m-sequence shifted in time.

Due to the long VEP response time, and possible overlap of the signal between segments, the technique as disclosed in U.S. Pat. No. 4,846,567(Sutter) requires the use of long m-sequences. The method described by Sutter does not allow the observation of responses during the recording, but only displays the product of cross-correlations at the end of the test when the entire m-sequence is finished. This property is a significant limitation since in clinical testing it is desirable to observe responses constantly during the recording procedure. In cases where the signal is unsatisfactory, recording time is wasted. In cases where the subject has a limited ability to co-operate and fixate on the screen target (eg children, elderly patients), short recording sequences are essential, as are frequent checking of the quality of each segment before it is included in the data With short recording sequences it is possible to avoid unnecessarily long recording times in cases where the signal is reliable, to stop the recording without loss of data if the patient fatigues, and allow additional runs to be added in when the response is noisy.

For example, consider the case of recording a multifocal VEP with 60 segments or 120 segments of visual field stimulated. With the method described by Sutter (above) using the same m-sequences for all segments of the visual field shifted in time, it is necessary to allow at least 500 msec, preferably 1000 msec, between segments to avoid overlap and contamination of signals. With a 75Hz frame rate at least 2250 code elements are required for 500 msec, and 4500 code elements for 1000 msec. Since m-sequences only come in predefined lengths of $2^n-1$, the shortest possible m-sequence required will be 2047 and 4095 elements of code respectively. This will result in recording times of approx 1 minute and 2 minutes respectively for 60 segments of visual field, 2 minutes to 4 minutes for 120 segments of field. Further increases in the number of field elements stimulated would require even greater minimum recording times before the results could be assessed in real time. Sutter alludes to the use of 255 segments or more in recording, which would be extremely useful clinically, but it would require at least 8 minutes of recording before any data could be accessed. Also, U.S. Pat. No. 5,539,482 (James & Maddess) disclosed a system whereby the contrast of each zone was modulated with a different respective temporal frequency. Each of the stimulus signals applied to each zone is orthogonal in time to the visual signals applied to all other zones such that the composition of the response into the components may be computed by Fourier transforms. The disadvantage with this method is that only a limited number of zones can be handled.

It is therefore an object of this invention to provide a method for the rapid objective measurement of the visual field based on simultaneous use of different stimulating sequences at each part of the field, where data can be readily assessed at short intervals during the recording.

Meaning of Terms

In this specification and claims the following terms have the meanings as set out:

"Cross-correlation": Cross-correlation can be described as comparison of two sequences $A=[a_0, a_1, \ldots a_{N-1}]$ and $B=[b_0, b_1, \ldots b_{N-1}]$ to determine how much they correspond with one another. If sequence B is cyclically shifted by i elements, the cross-correlation r, can be calculated as follows $$r_i = \sum_{n=0}^{N-1} a_n b_{n-1}$$

"Auto-correlation": Auto-correlation can be described as comparison of sequence A=[$a_O$, $a_1$, ... $a_{N-1}$] and it's own delayed copy to determine how much different phases of the same sequence differ one from another. If a copy of sequence A is cyclically shifted by i elements, the auto-correlation $r_i$ can be calculated as follows $$r_i = \sum_{n=0}^{N-1} a_n a_{n+i}$$

An acceptable level of cross-correlation for clinical testing is less than 6% of the auto-correlation peak (N−1) for a sequence of length 1023 samples or more.

"M-sequence": M-sequence can be created by applying a single shift register with a number of specifically selected feedback-taps. If the shift register size is n then the length of the m-sequence is equal to $2^n-1$. More detailed introduction in m-sequences can be found in MacWilliams & Sloane, "Pseduo-Random Sequences and Arrays", Proc IEEE, Vol 64, No 12, December 1976, pp 1715–1729.

"Gold family of binary sequences": The family of the Gold sequences can be generated as a product of two m-sequences which form a "preferred pair". So called "preferred pair" is a combination of m-sequences for which the cross-correlation shows only 3 different values: 1, $-2^{'m+1_1/}2-1$, $2^{'m+1_1/2}+1$. Different members of the family may be generated by giving one of the codes a delay with respect to the other code. Information on Gold codes can be obtained from Sarwate & Pursley, "Crosscorrelation Properties of Pseudorandom and Related Sequences", Proc IEEE, Vol 68, No 5, May 1980, pp593–619.

"Kasami family of binary sequences": A family of the Kasami sequences can be obtained by combining Gold codes with decimated version of one of the two m-sequences that form the Gold sequence described in the previous paragraph. Information on Kasami codes may be obtained from Sarwate & Pursley above.

DISCLOSURE OF THE INVENTION

The current invention attempts to address the limitations of existing systems discussed above, by using different stimulating sequences for each part of the visual field. Instead of a single m-sequence, a family of binary sequences is employed with a unique sequence for each part of the field. These sequences have low cross-correlation properties between family members and good auto-correlation properties. Ideally, the auto-correlation function of any sequence is impulse valued and cross-correlation values are zeroes for any pair of the sequences of the family. Unfortunately there is no family of binary sequences with such ideal correlation properties. For practical purposes, various families of sequences can be used such as Kasami, Gold etc. They have acceptable cross-correlation and auto-correlation properties to separate responses from different parts of visual field with sufficient accuracy. The correlation properties of Gold and Kasami families are discussed below.

Using these sequences all parts of the visual field are stimulated simultaneously according to different sequences from the family. At the completion of each recording run, which is equal the whole period of the sequence, results can be calculated and displayed with progressive averaging. Each run can be as short as 12 seconds (or shorter if required). An advantage of this technique is the ability to monitor the responses after each short run and to decide if the last run provides meaningful results and if more runs are required. This is accomplished by visual inspection, based on the experience of the operator and depends on, for example the clarity of the measurement signals and acceptably low level of noise. Another advantage is that increasing the number of stimulated segments does not increase the recording time required. For example, using the Gold sequence family for recording a pattern VEP, as many as 1025 segments of visual field can be stimulated simultaneously using a sequence of 1023 elements of code, requiring only 12 seconds of recording time The equivalent number of stimuli using the Sutter system would require 16 minutes of data recording before any results could be assessed.

The stimulus used can be a pattern or flash, and can therefore be adapted to multifocal electroretinogram (ERG) recording.

According to a first aspect of this invention there is provided a method of providing a visual reaction map of at least part of the visual field of an eye of a subject, the method comprising:

(a) presenting to said visual field a plurality of segments each of the segments comprising an individually activated image;

(b) changing each of said individually activated images in each of said segments according to a binary sequence each of said images being changed in a different way from all other of said images whereby the changing of one of said images does not substantially correlate with the changing of any of the other of said images;

(c) detecting measurement signals in said subject while said visual field is presented with said changing;

(d) correlating said measurement signals with each of the binary sequences used to activate each of said individual segments; and (e) providing said visual reaction map from said correlating.

Generally the method further comprises (f) determining from said visual reaction map whether said eye has one or more areas of defective vision.

According to a second aspect of this invention there is provided a system for providing a visual reaction map of at least part of the visual field of an eye of a subject, the system comprising:

(a) means for presenting to said visual field a plurality of segments each of the segments comprising an individually activated image;

(b) means for changing each of said individually activated images in each of said segments according to a binary sequence each of said images being changed in a different way from all other of said images whereby the changing of one of said images does not substantially correlate with the changing of any of the other of said images;

(c) means for detecting measurement signals in said subject while the visual field of the eye of said subject is presented with individually activated images in each of said segments which are changed according to a binary sequence each of said images being changed in a different way from all other of said images whereby the changing of one of said images does not substantially correlate with the changing of any of the other of said images;

(d) means for correlating said measurement signals with each of the binary sequences used to activate each of said images in said segments; and (e) means for providing said visual reaction map from said correlating.

Suitably, the individually activated images are computer generated.

According to a third aspect of this invention there is provided a method for assessing extent of visual field loss in a patient suffering from a neuro-opthalmic disorder, comprising providing a visual reaction map in accordance with the method of the first aspect of this invention and assessing the extent of visual field loss from said visual reaction map.

The binary sequences may be, for example Gold, Kasami, Bent or the like. Any binary sequence which enables the changing of each of the individually activated images in each of the segments being changed in a different way from all other of the images whereby the changing of one of the images does not substantially correlate with the changing of any of the other images, may be employed. Preferably, the sequences are Gold and Kasami. Details of these sequences are set out in Table 1.

can be used. For practical purposes, the shortest sequence consists of 1023 elements of code which results in 13.6 sec of recording time at 75 Hz.

There is also no increase in recording time associated with increased number of areas of the visual field stimulated, which is due to the fact that the families of sequences have a large enough number of the members. For instance, the Gold family has 1025 members for the sequence of 1023 elements of code, which means that up to 1025 areas of the visual field can be stimulated simultaneously.

Each segment of the image is a pattern which is representative of the visual reaction of that pan of the eye that corresponds to that segment. The pattern may be a black and white pattern, and gray and black pattern, a color pattern or other suitable pattern e.g. a pattern reversal. The image in each segment may also produce a diffuse white illumination and may change in brightness. Each image in each segment may also be a diffuse color illumination and the sequences may produce a change in color.

Typically, the measurement signals are detected by means of electrodes which are placed on the head or eyelids of the subject. The measurement signals correspond to visually evoked potentials. These electrodes are placed thus by methods known in the art of ERG recording. The method of the invention usually involves placing electrodes on the head or eyelids of the subject and detecting the measurement signals via these electrodes.

TABLE 1

| Family of binary sequences | Sequence length | Maximum value of cross-correlation | Number of sequences in the family | Reference |
| --- | --- | --- | --- | --- |
| Gold Codes | $N = 2^n - 1$, $n \equiv 1 \mod 2$ | $\dfrac{\sqrt{2(N+1)} + 1}{N}$ | $N + 2$ | Gold R. Optimal binary sequences for spread spectrum |
|  | $N = 2^n - 1$, $n \equiv 2 \mod 4$ | $\dfrac{2\sqrt{N+1} + 1}{N}$ | $N + 2$ | multiplexing, IEEE Trans. - 1967. - V.IT-13, No 4, p. 619–621. |
| Small set of Kasami Sequences | $N = 2^{2n} - 1$ $n \geq 2$ | $\dfrac{\sqrt{N+1} + 1}{N}$ | $\sqrt{N+1}$ | Sarwate & Pursley, "Crosscorrelation Properties of Pseudorandom and Related Sequences", Proc IEEE, Vol 68, No 5, May 1980, p. 593–619. |
| Bent-function sequences | $N = 2^{2n} - 1$, $n \equiv 0 \mod 2$ | $\dfrac{\sqrt{N+1} + 1}{N}$ | $\sqrt{N+1}$ | Olsen J. D., Scholtz R. A., Welch L. R. Bent-function sequences, IEEE Trans. 1982. - V.IT-28 No 6. - p. 858–864. |
| Combined family of Kasami and Bent-functions sequences | $N = 2^{2n} - 1$, $n \equiv 0 \mod 2$ | $\dfrac{\sqrt{N+1} + 1}{N}$ | $2\sqrt{N+1} - 1$ | Kamaletdinov, B. Zh. Optimum set of binary sequences based on combination of ensembles of Kasami and Bent-function sequences. Problems of Information Transmission, 1988, v.23, No 2, p. 104–107. |

With regard to step (b) in both aspects of the invention set out above, the use of the different binary sequences for changing the image within each said segment which belongs to a family of sequences with acceptably low cross-correlation between members of said family and an impulse valued auto-correlation function confers a significant advantage for clinical application. Due to low cross-correlation between members of the said family there is practically no cross-talk between responses derived from stimulation of different areas of the visual field. This allows the stimulation of all parts of the tested visual field simultaneously with no time shift between the segments. Therefore, sequences as short as 127 elements of code (1.7 sec at 75 Hz frame rate)

The visual reaction map is any visual reaction map which suitably displays measurement signals generated by the above-described means. For example, the visual reaction map is suitably a Humphrey Visual Field Map. Generally the visual reaction map shows significant reduction in amplitude of visual reaction in areas of defective vision as compared to amplitude of visual reaction in areas of normal vision.

The intensity of the plurality of segments presented to the visual field is sufficient to result in detectable measurement signals but not of an intensity that would cause damage to the exposed eye of the subject The intensities used in practising this invention are well known in this art.

In practising the methods of this invention, it is possible to provide a visual reaction map using one run only.

However, it is preferable that more than one run is carried out (e.g. 2, 3, 4, 5, 6, 7, 8, 9, 10 or more runs). As the number of runs increases, the runs are progressively averaged. The result of this progressive average is that as the number of runs increases, a visual reaction map is produced with decreasing levels of noise. Referring to the dicussion of U.S. Pat. No. 4,846,567(Sutter) above, that method requires long recording times and the person carrying out the test can only see the result of the test at the end of the recording time. The significance of the shorter recording times of this invention and the ability to carry out the test a number of times and average those results is that as mentioned, it is possible to carry out one run and it is possible to observe the results as the test is progressing and finally, even repeating the test a number of times still allows a shorter time of subjecting the patient to the test than the prior art methods such as those described in Sutter. Typically, six to eight runs may be performed, each run lasting approximately 12 seconds or less. The image is displayed on any suitable display that can present information derived from a suitable binary sequence (e.g. a monitor such as a computer monitor or screen onto which the image in projected, a hologram etc.)

When analyzing the measurement signals from the subject, a correlation between these measurement signals and the binary sequence used to activate the individual segment of the computer generated image is calculated to separate a response for that segment from other segment responses. As a result, a visual reaction map of the visual field is produced as a set of cross-correlation functions between the signal and the members of the family used to stimulate individual segments of the computer generated image. The map thus derived, is a representation of the vision of a subject in each part of the visual field.

For example, where a person is suffering from glaucoma, the results show reductions in areas of defective vision, known as scotomas. Detection and monitoring of scotomas is vital in the diagnosis and management of glaucoma and other neuro-ophthalmic disorders affecting the visual system.

BRIEF DESCRIPTION OF THE DRAWINGS

A number of embodiments of the present invention will now be described with reference to the drawings in which.

DESCRIPTION OF THE INVENTION

Figure 8:
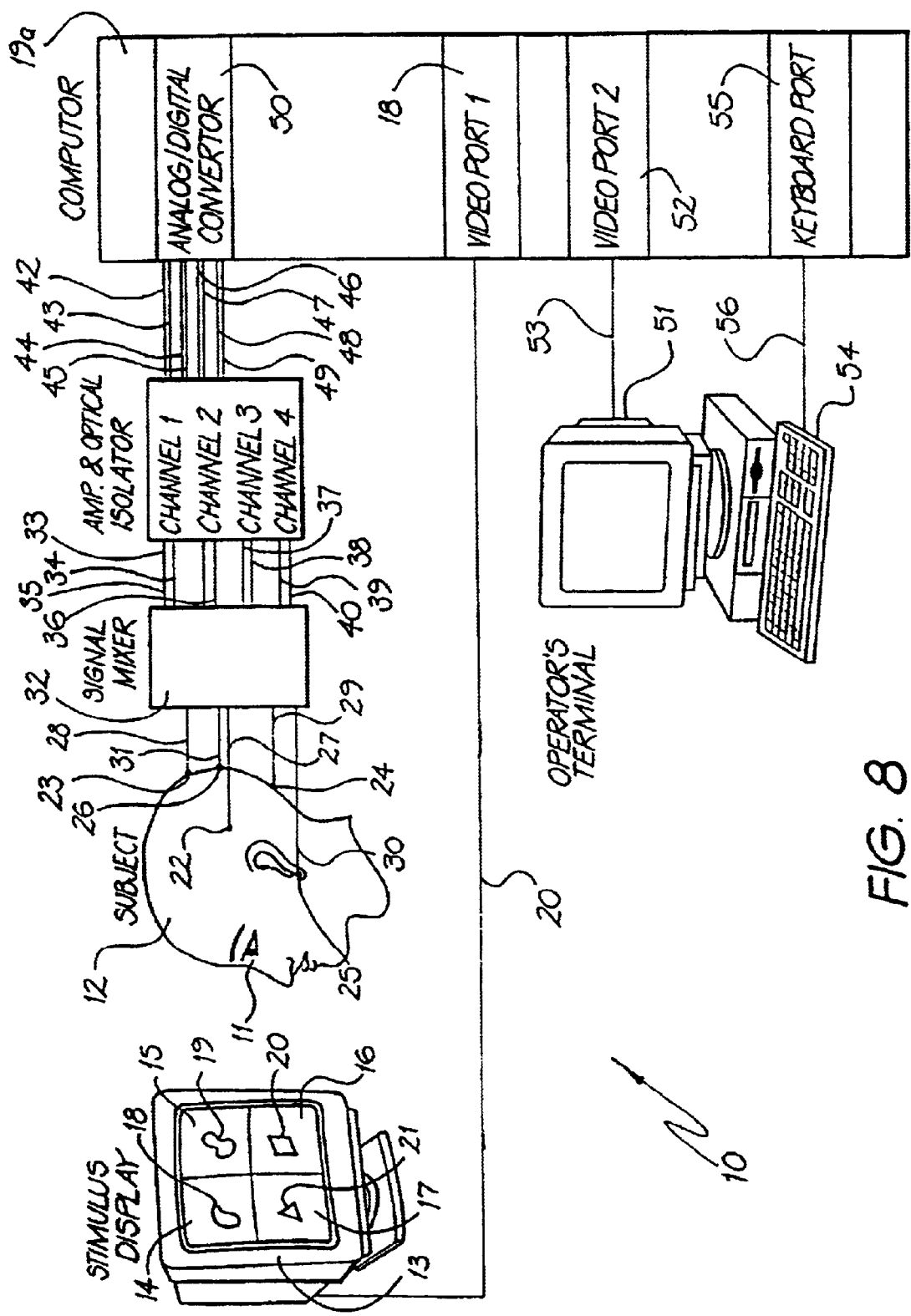
FIG. 8 is a schematic diagram of the objective visual field testing system.

FIG. 8 depicts a system 10 for providing a visual reaction map of at least part of the visual field of eye 11 of subject 12. System 10 has computer display 13 for presenting to the visual field of eye 11 a plurality of segments 14, 15, 16 and 17 each of segments 14, 15, 16 and 17 comprising an individually activated image 18, 19, 20 and 21. Display 13 is connected to video port 122 of computer 19 via line 20. Computer 19 is programmed to change each of the individually activated images in each of segments 14, 15, 16 and 17 according to a binary sequence each of the images 18, 19, 20 and 21 being changed in a different way from all other of the images whereby the changing of one of the images 18, 19, 20 and 21 does not substantially correlate with the changing of any of the other of the images 18, 19, 20 and 21. System 10 includes electrodes 22, 23, 24, 25 and 26 which are connected to signal mixer 32 via lines 27, 28, 29, 30 and 31 and amplifier and optical isolator 41 which is linked to signal mixer 32 via lines 33–40 and computer 19 which is linked to amplifier and optical isolator 41 via analog/digital convener 50 via lines 42–49 for detecting measurement signals in subject 12. Measurement signals in subject 12 are detected while the visual field of eye 11 of subject 12 is presented with individually activated images 18, 19, 20 and 21 in each of segments 14, 15, 16 and 17 which are changed according to a binary sequence each of images 18, 19, 20 and 21 being changed in a different way from all other of images 18, 19, 20 and 21 whereby the changing of one of images 18, 19, 20 and 21 does not substantially correlate with the changing of any of the other of said images 18, 19, 20 and 21. Computer 19 is programmed to correlate the measurement signals with each of the binary sequences used to activate each of said images 18, 19, 20 and 21 in each of said segments 14, 15, 16 and 17. Operator's terminal 51 which is linked to computer 19 via video port 52 and line 53 and associated keyboard 54 which is linked to computer 19 via keyboard port 55 and line 56 provide means for displaying the visual reaction map from correlating the measurement signals with each of the binary sequences used to activate each of said images 18, 19, 20 and 21 in each of said segments 14, 15, 16 and 17.

In use a visual reaction map of at least part of the visual field of eye 11 of subject 12 is determined as follows. The visual field of eye 11 is presented with plurality of segments 14, 15, 16 and 17 comprising individually activated images 18, 19, 20 and 21 respectively. Simultaneously as the visual field of eye 11 is presented with plurality of segments 14, 15, 16 and 17 each of individually activated images 18, 19, 20 and 21 in each of segments 14, 15, 16 and 17 are changed by computer 19 according to a binary sequence each of images 18, 19, 20 and 21 being changed in a different way from all other of images 18, 19, 20 and 21 whereby the changing of one of said images 18, 19, 20 and 21 does not substantially correlate with the changing of any of the other of said images 18, 19, 20 and 21. Each of individually activated images 18, 19, 20 and 21 in each of segments 14, 15, 16 and 17 are changed by computer 19a which is appropriately programmed so as to change each of individually activated images 18, 19, 20 and 21 in each of segments 14, 15, 16 and 17 by a different binary sequence, each of the different binary sequences having low cross-correlation with the other of the different binary sequences. The different binary sequences generally belong to a family of binary sequences with acceptably low cross-correlation between members of said family. Each of individually activated images 18, 19, 20 and 21 is changed in a different way from each other image, wherein the changes do not substantially correlate with each other. Measurement signals are collected in subject 12 via electrodes placed on the head of the subject 12 while the visual field of eye 11 is presented with changing individually activated images 18, 19, 20 and 21. The measurement signals are correlated with each of the binary sequences used to activate each of individually activated images 18, 19, 20 and 21 in each of segments 14, 15, 16 and 17 and a resultant visual reaction map which is determined by computer 19a from the correlation is displayed on operators terminal 51. The operator then usually determines from the visual reaction map whether eye 11 has one or more areas of defective vision.

Figure 1:
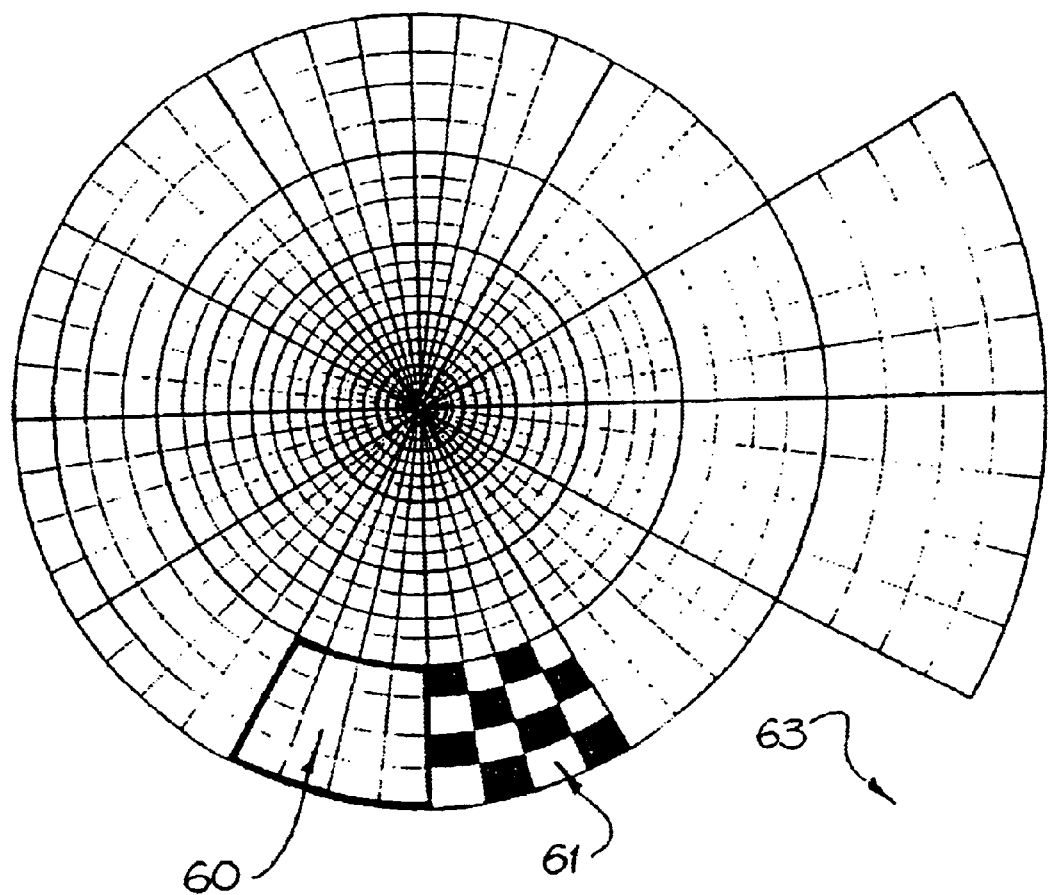
FIG. 1 is a representation of the stimulus pattern used for VEP recording.

The binary codes can be used to control segments within a pattern stimulus such as in FIG. 1. The stimulus shown on FIG. 1 is designed to stimulate the visual field to produce approximately equal signals from all parts. The size of the segments (the dimensions of one of which 60 is illustrated by a border for convenience) and the enclosed checks (an example of which is denoted by reference numeral 61) is gradually increased towards the periphery (the direction of which is illustrated by arrow 63). This is known as cortical scaling. The stimulus is divided into 58 segments. Each segment contains 16 checks which alternate according to different sequence patterns applied to each segment. The eye of the subject is activated by this stimulus and in order to pick up a resultant signal, which is known as a measurement signal, electrodes are placed on the head of the subject. There are K segments on the stimulus and each segment is modulated with the unique spreading sequence $C^{(k)}$ of length N from a family of binary pseudo noise codes, where each symbol $C_n^{(k)}$ of the sequence can be 1 or −1

$$C^{(1)} = [c_0^{(1)}, c_1^{(1)}, \ldots c_{N-1}^{(1)}]$$

$$C^{(2)} = [c_0^{(2)}, c_1^{(2)}, \ldots c_{N-1}^{(2)}]$$

$$\ldots$$

$$C^{(k)} = [c_0^{(k)}, c_1^{(k)}, \ldots c_{N-1}^{(k)}]$$

The family of spreading sequences has the cross-correlation properties:

$$\sum_{n=0}^{N-1} c_n^{(k)} c_{n+i}^{(j)} \approx \begin{cases} N & k=j, i=0 \\ 0 & \text{otherwise} \end{cases},$$

which provides a family of K sequences with zero cross-correlations and impulse-valued auto-correlations.

In a first basic modulation method, the pattern of the segment reverses if code element $c_n^{(k)} = 1$, and is held to the same pattern if $c_n^{(k)} = -1$. A response is generated for positive elements of the sequence.

Turning to the electrodes which are placed on the head of the subject to detect a measurement signal, two electrodes are suitably positioned along the midline 2 cm above and 4 cm below the inion. Two additional electrodes are suitably placed 4 cm on either side of the inion. Four bipolar channels of different orientation are used. The measurement signal then is amplified and converted in digital form. Raw data $[a_0, a_1, \ldots a_{N-1}]$ are stored in computer memory for calculation of the response traces later when the recording run finishes. M is a number of collected samples.

Data processing can be done in two stages. In a first processing stage, derived signals $[b_0, b_1, \ldots b_T]$ are obtained from the raw data:

$$b_0 = [b_{0,0}, b_{0,1}, \ldots b_{0,N-1}]$$

$$b_1 = [b_{1,0}, b_{1,1}, \ldots b_{1,N-1}]$$

$$\ldots$$

$$b_T = [b_{T,0}, b_{T,1}, \ldots b_{T,N-1}]$$

$$b_{t,n} = a_{t+nS},$$

where t=sample number from the beginning of a code element, i=code element number, S=number of samples per code element.

T maximum duration of the response.

Figure 2:
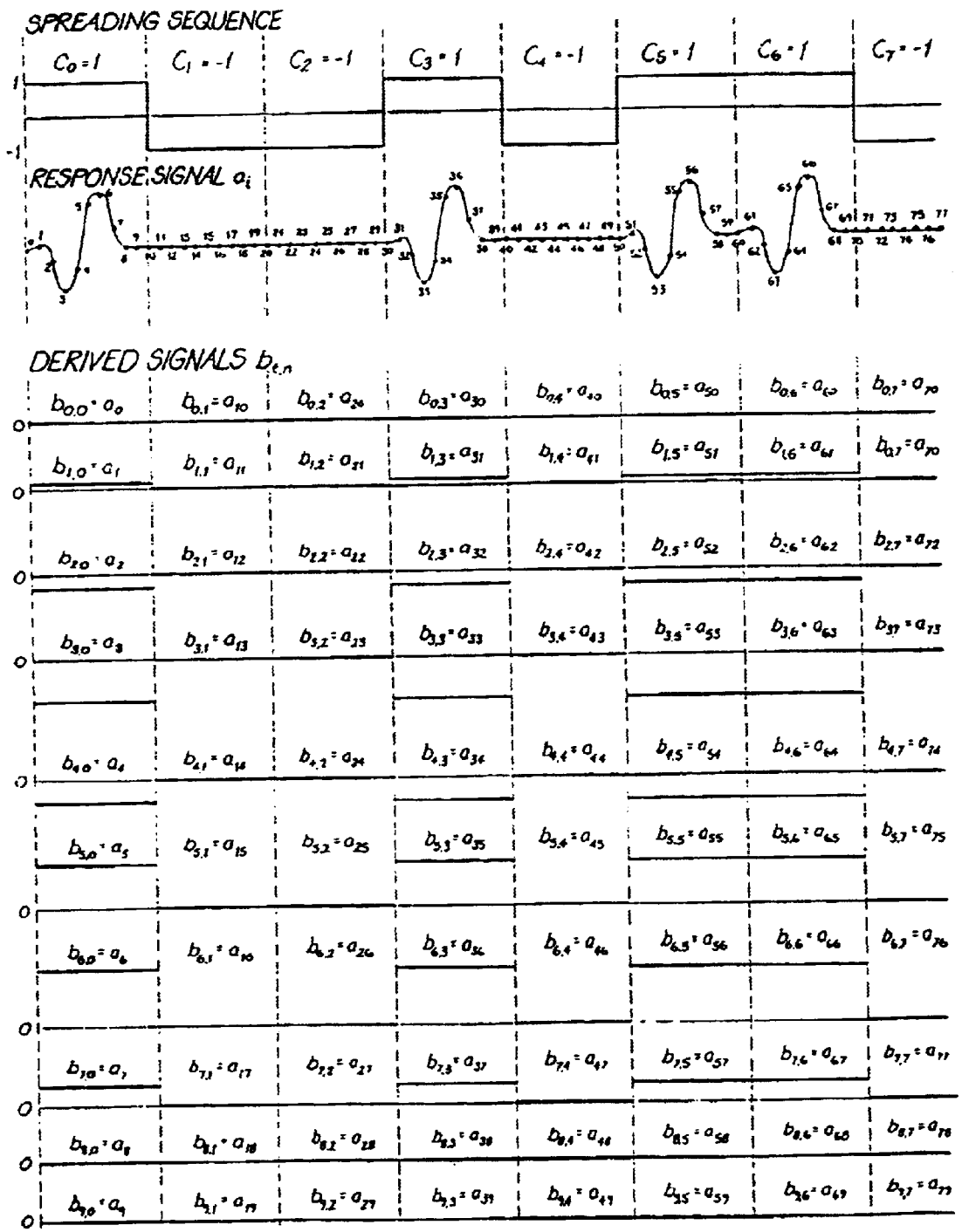
FIG. 2 is an example of a segment activation where responses are generated for positive code elements.

This case is illustrated in FIG. 2 where S=10 and T=10. The upper row represents a fragment (8 elements) of the code. The checkerboard reverses in polarity when the code element (C)=1 and stays the same when C=−1. The second row shows hypothetical responses to checkerboard reversal. Dots on the trace line represent sampling of the raw signal. During each frame the response is sampled 10 times. The matrix below the trace shows how the derived signal for those 8 elements of the code is calculated. For instance, to derive the first point of the response the operational algorithm selects every tenth sample of the raw data (a0, a10, a20 . . . a70).

A second modulation method produces responses from both the positive and the negative code elements. The segment changes pattern at the beginning of the code element if the element is positive or reverse pattern at the middle of the code symbol otherwise. The run duration is two times longer for the second method. In this case the derived signals are calculated as follows:

$$b_{t,n} = a_{t+nS} - a_{t+nS+S/2}$$

Figure 3:
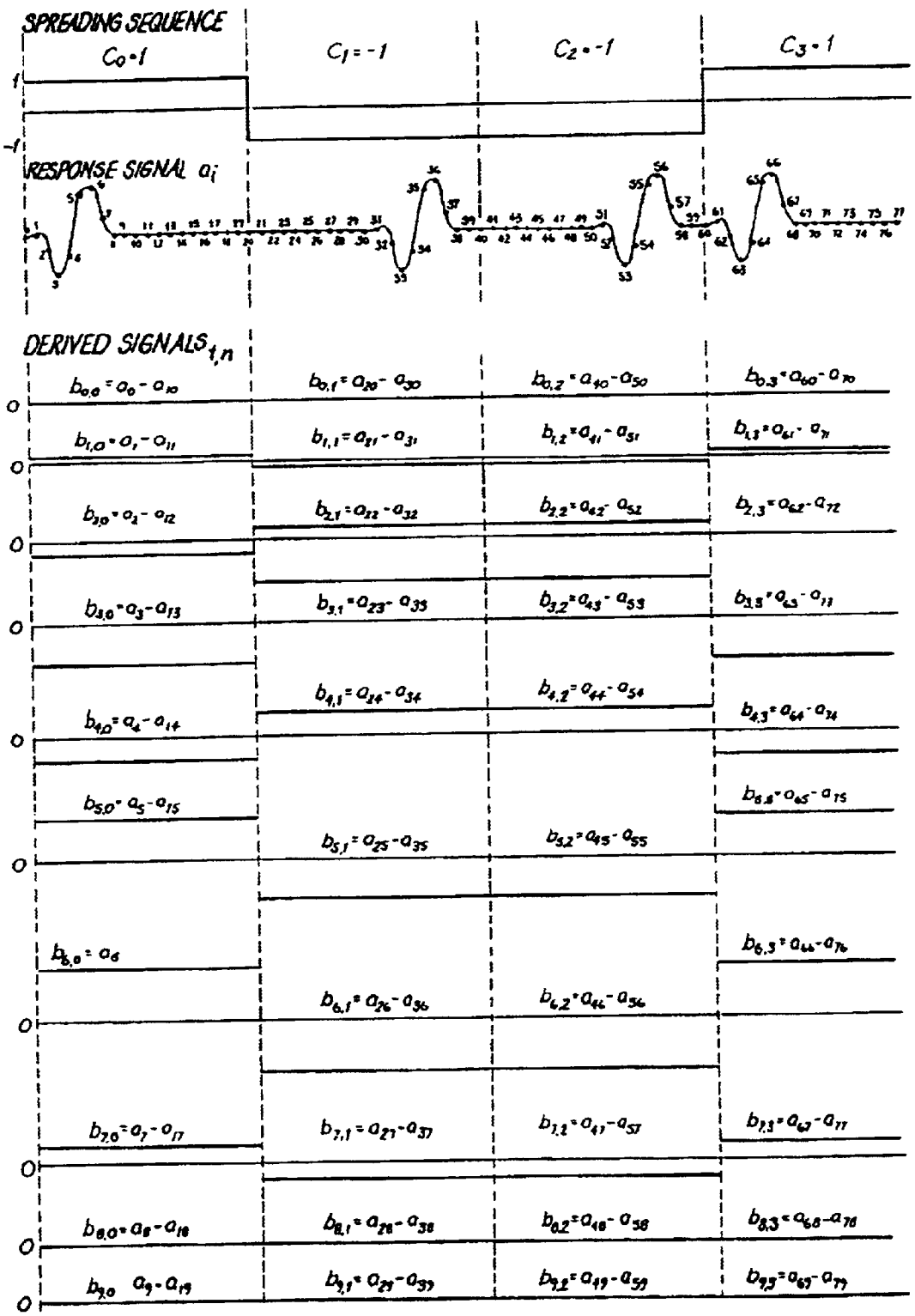
FIG. 3 is an example of a segment activation where responses are generated for positive and negative code elements.

FIG. 3 shows details of the second type of modulation where S=20 and T=10. In comparison with the first type of modulation shown in FIG. 2 the checkerboard pattern reverses not only at C=1, but also at C=−1. In the case of the latter the reversal takes place in the middle of the element of code. To calculate the first point of the response, the difference between the first and tenth sampling points of the element of code is determined and used by the operational algorithm.

A waveform of the responses generated by the pattern reversal of a segment stays the same for the run duration. If the second type of modulation is used, the response signal for segment k is:

$$b_t^{(k)} = r_t^{(k)} c_n^{(k)},$$

where $r^{(k)}$ is the response waveform for segment k. When all segments are simultaneously activated a combined response signal $B_n$ can be presented as a sum of the segment signals and a measurement noise $w_n$:

$$B_{t,n} = \sum_{k=1}^{K} b_{t,n}^{(k)} c_n^{(k)} + w_n$$

The measurement noise can be modeled as a normal (Gaussian) random variable.

At the second processing stage response traces are computed for every segment. The response trace for segment k is calculated as a set of cross-correlations $[y_0^{(k)}, y_1^{(k)}, \ldots y_Y^{(k)}]$:

$$y_t^{(k)} = \sum_{n=0}^{N-1} B_{t,n} c_n^{(k)}$$

The cross-correlation for segment k=1(for example) gives the following result:

$$y_t^{(l)} = r_t^l \sum_{n=0}^{N-1} (c_n^{(l)})^2 + \sum_{k=2}^{K} r_t^{(k)} \sum_{n=0}^{N-1} c_n^{(k)} c_n^{(l)} + \sum_{n=0}^{N-1} w_n c_n^{(l)}$$

Using the cross-correlation property, $$y_t^{(l)} \approx N r_t^{(l)} + 0 + \sum_{n=0}^{N-1} w_n c_n^{(l)},$$

between the members of the family, allows separation of responses from different segments of the stimulus when all segments are activated simultaneously.

Figure 4:
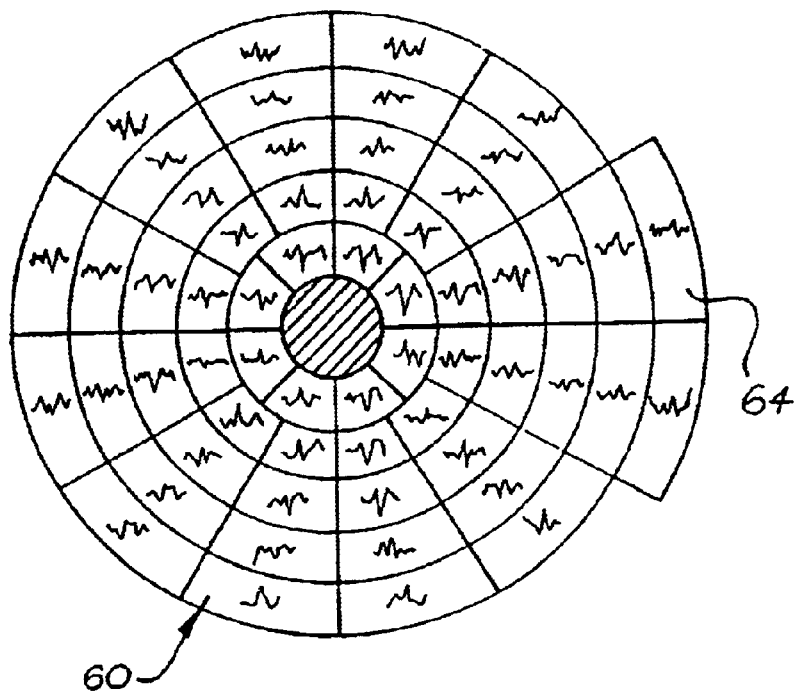
FIG. 4 is an example of a multifocal VEP trace array after 1 run of 65 seconds.
Figure 5:
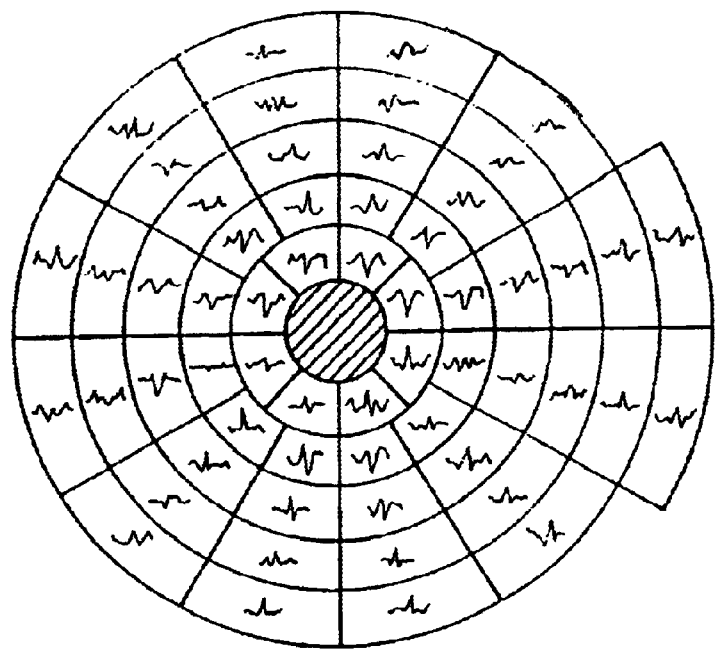
FIG. 5 is an example of the same trace array after 2 runs.
Figure 6:
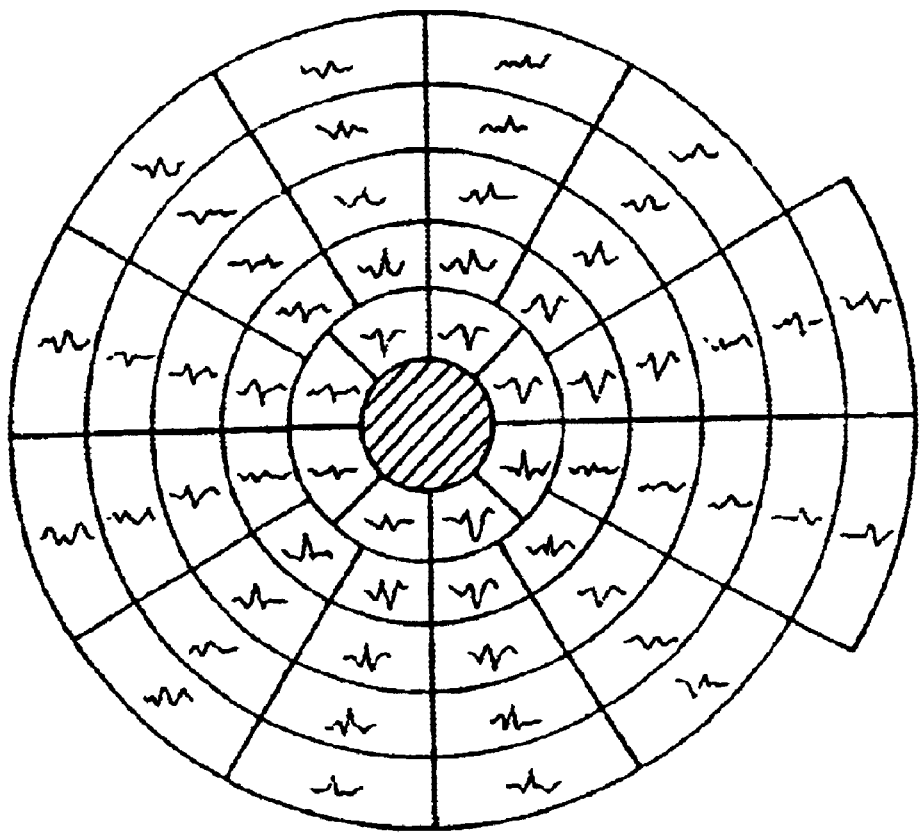
FIG. 6 is an example of the same trace array after 6 runs.

The response traces are computed for all segments and appears on the computer monitor. Examples of response trace arrays are shown in FIGS. 4–6. These are described in detail below.

Usually response traces delivered from a single run are noisy. A number of runs are preferably performed to increase the quality of the traces. Progressive averaging is used to filter response traces from the noise:

$$y_t^{(k)}[m] = \frac{m-1}{m} y_t^{(k)}[m-1] + \frac{1}{m} y_t^{(k)},$$

where m =run number starting from 1,
  $y_t^{(k)}[m]$ =current averaged trace,
  $y_t^{(k)}[m-1]$ =previous averaged trace
  $y_t^{(k)}$ =trace delivered from current run.

An example of progressive averaging is exhibited in FIGS. 4, 5 and 6, where trace arrays are shown after 1, 2 and 6 runs. The trace array represents the maximal response recorded for each segment of the visual field from any of the four recording channels. The printout automatically scales the responses equally to fit into the graphic display shown in the figures. The field location is the same as for FIG. 1 except that for graphics purposes the inner segments are shown enlarged to fit the signal into the graphic using the same amplitude scale. The inner points actually represent smaller areas of the visual field than are seen in the trace array.

In the recordings seen in FIGS. 4 to 6, the run duration was set at 65 seconds. After just one run the signals (an example of a measurement signal being denoted as reference numeral 64) are readily identified confirming satisfactory recording conditions with some greater noise levels in the horizontal channel. In the clinical scenario this run could then be accepted or rejected with further attention to the electrode positions and contacts for the horizontal channel. A further improvement in the quality of the traces observed after 2 runs, as seen in FIG. 5. FIG. 6 shows the trace array derived after six runs. The quality of the trace is sufficient for analysis. It would not be necessary to continue recording since the amplitudes have stabilised and background noise levels are low.

Movements of the subject's body, while a run is in progress, can introduce an unwanted distortion of the response. The run can be rejected if the trace is contaminated. In this case previous averaged traces are used again to calculate averaged traces after the next run.

Real families of binary pseudo noise sequences have non-zero cross-correlations between the family members. This does not allow for perfect separation of responses from different segments. For example, maximum cross-correlation values V of well known Kasami and Gold binary sequences are:

$$|V_{Kasami}| = \frac{\sqrt{N+1}+1}{N}, \quad N = 2^{3p}-1, \quad p > 2$$

$$|V_{Gold}| = \frac{2\sqrt{N+1}+1}{N}, \quad N = 2^p - 1, \quad p = 2 \bmod 4$$

$$|V_{Gold}| = \frac{\sqrt{2(N+1)}+1}{N}, \quad N = 2^p - 1, \quad p = 1 \bmod 2$$

As can be determined from the above, the maximum cross-correlation is less than 6% of auto-correlation peak (N−1) for a sequence of length 1023 samples or more. Such a level of cross-relation between different segments is acceptable for practical purposes.

Cross-contamination of segments can be greatly reduced if a different family member controls the same segment in each different run of a recording series. The reduction can be explained by the fact that the result of the crosscorrelation function for any pair of members of the family differs from that of any another pair. The cross-contamination can therefore be viewed as pseudo noise process formed as a superposition of the crosscorrelation waveforms of the resulting cross-contamination noise depend on the correlations properties of the family, and they are different for various members. The level of cross talk noise may be reduced by averaging the cross-contamination noise waveforms of number of the family members. This can be achieved by allocating different sequences from the family members to the same segment each time a new run starts, with progressive averaging of the traces. For example, assume there are 58 segments and 8 runs to be collected. The first segment is modulated by the sequence 1 of the family for the first run. At the second run the second sequence of the family is used and so on Table 2 shows which family members are used to control segments for each run.

TABLE 2

| Segment | Run | | | | | | | |
|---|---|---|---|---|---|---|---|---|
| | 1 | 2 | 3 | 4 | 5 | 6 | 7 | 8 |
| 1 | 1 | 2 | 3 | 4 | 5 | 6 | 7 | 8 |
| 2 | 2 | 3 | 4 | 5 | 6 | 7 | 8 | 9 |
| 3 | 3 | 4 | 5 | 6 | 7 | 8 | 9 | 10 |
| 4 | 4 | 5 | 6 | 7 | 8 | 9 | 10 | 11 |
| 5 | 5 | 6 | 7 | 8 | 9 | 10 | 11 | 12 |
| 6 | 6 | 7 | 8 | 9 | 10 | 11 | 12 | 13 |
| 7 | 7 | 8 | 9 | 10 | 11 | 12 | 13 | 14 |
| . | . | . | . | . | . | . | . | . |
| . | . | . | . | . | . | . | . | . |
| . | . | . | . | . | . | . | . | . |
| 58 | 58 | 1 | 2 | 3 | 4 | 5 | 6 | 7 |

Figure 11A:
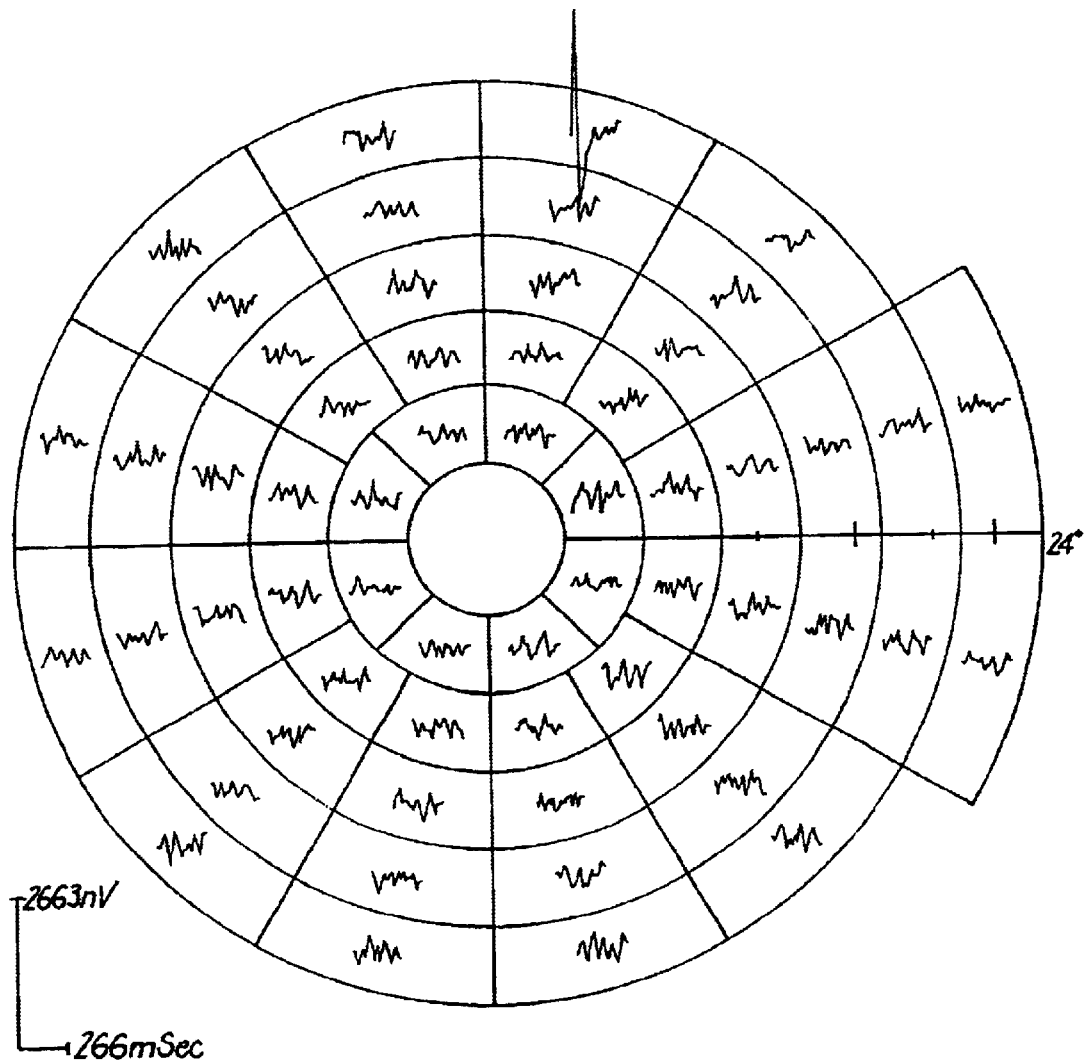
FIGS. 11(a), (b) and (c) are examples of cross-contamination noise reduction after 1, 3 and 8 runs respectively.
Figure 11B:
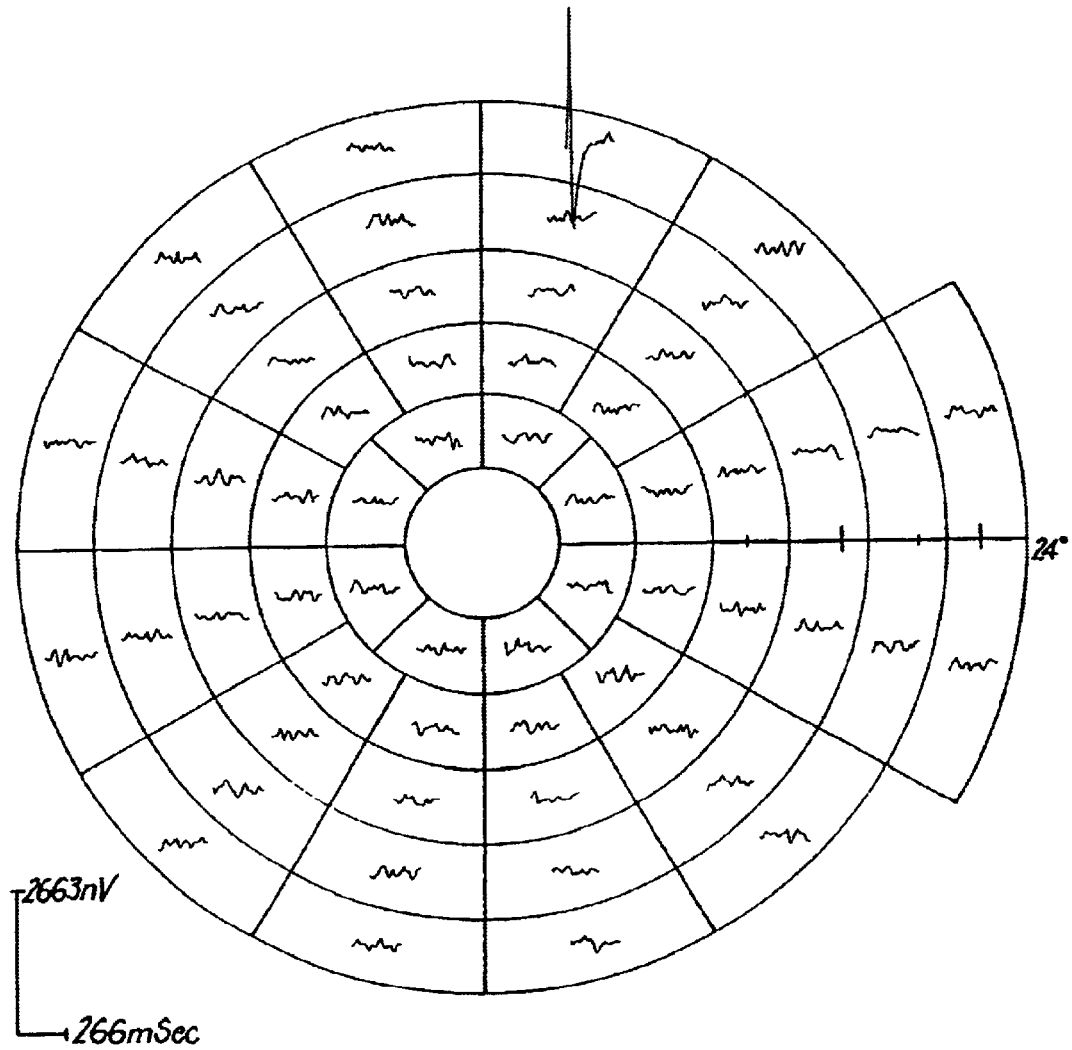
Figure 11C:
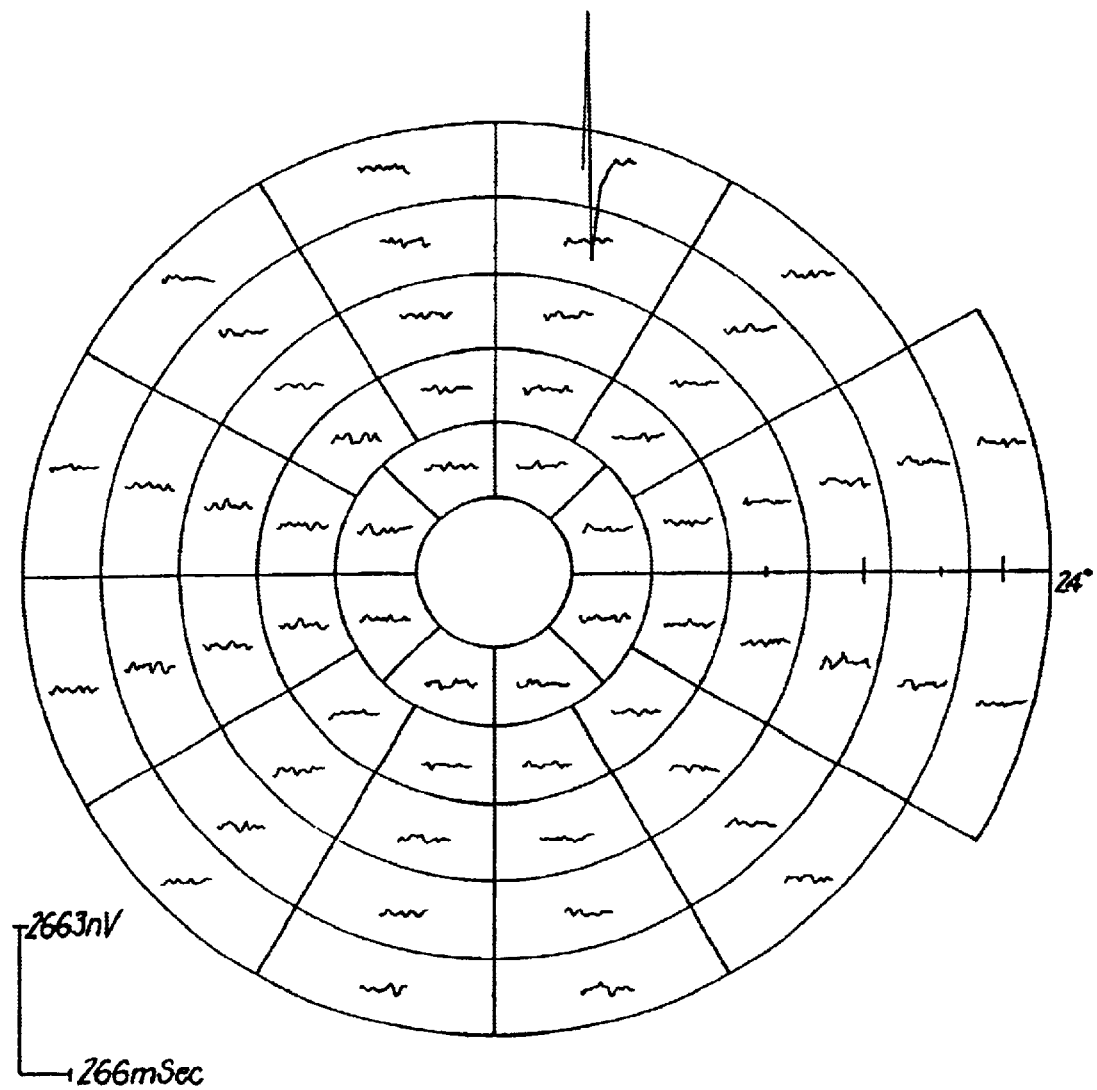

An example of averaging of the cross-contamination noise waveforms is shown in FIGS. 11a–11c. These show responses recorded from a photo diode connected to the amplifier instead of the subject (12) and signal mixer (32). The photo diode is pointed to one of the segments on the stimulus display. FIGS. 11a, 11b and 11c show traces after the first run, 3 runs and 8 runs respectively. A large spike indicated the segment the photo diode was pointed to. This demonstrates a significant reduction in the segment cross talk.

Clinical Application to 72 Year Old Male With Glaucoma

Figure 7A:
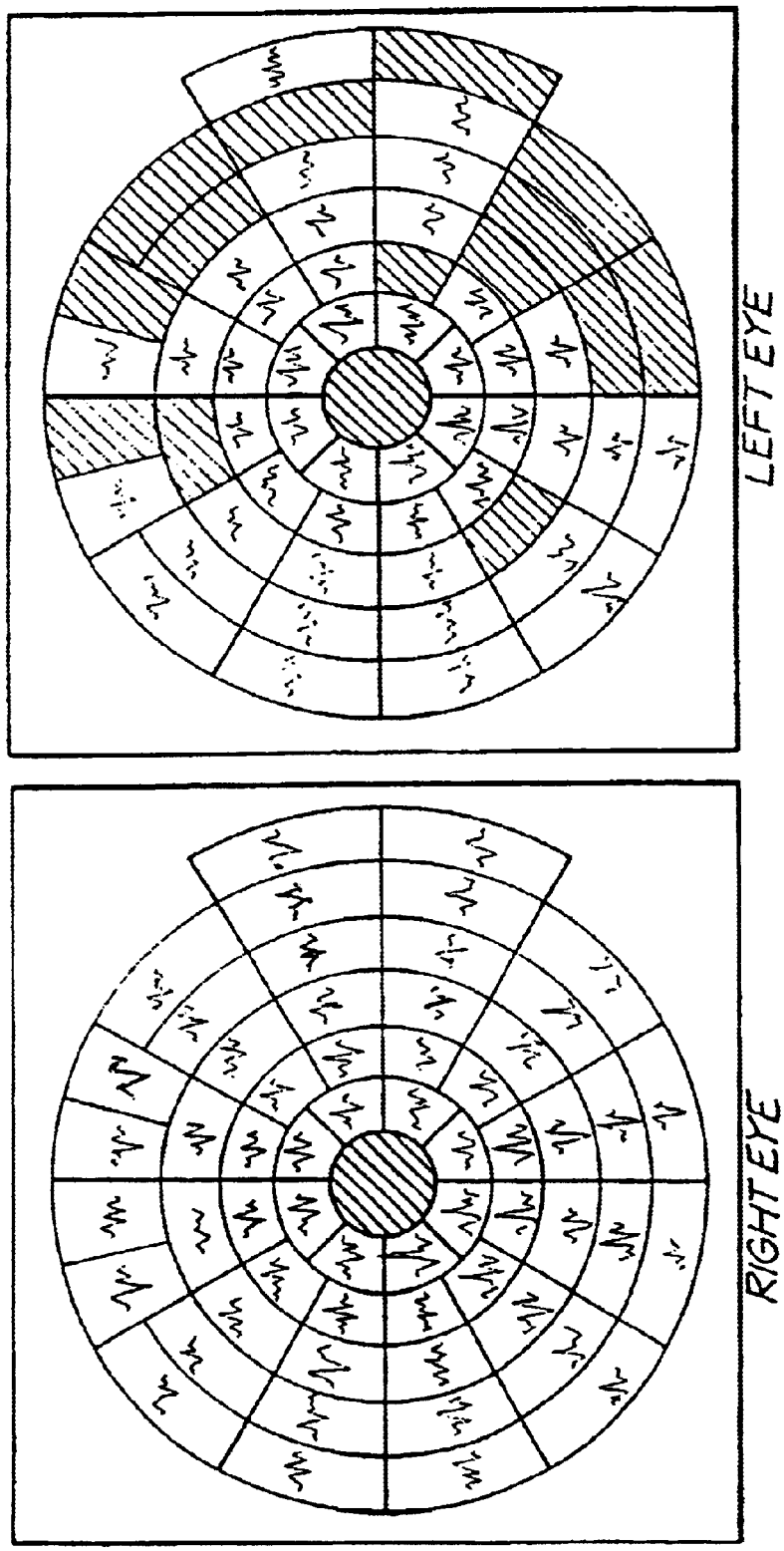
FIG. 7 is a clinical example of using the multifocal VEP recording in a glaucoma patients and consists of FIG. 7a which is a trace array from left and right eyes.
FIGS. 7b(i) and (ii) which shows the corresponding subjective Humphrey visual field printouts from the right and left eyes respectively.
Figure 7B:
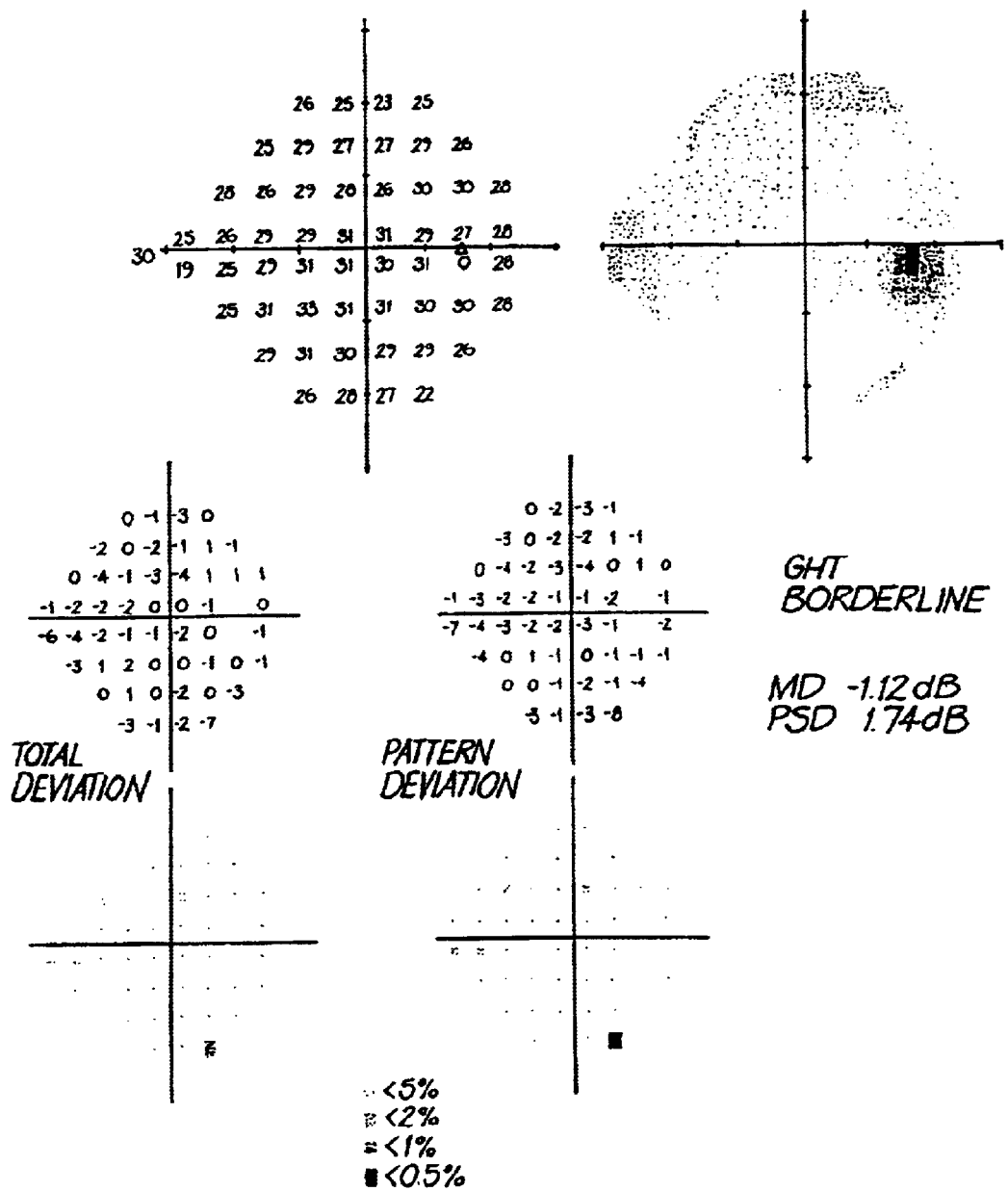

A clinical example of the correlation between results using the Humphrey visual field analyser (see Background Art) and the multifocal VEP recorded using the technique described above is shown in FIG. 7. The example shows responses recorded from a 72 year old male with previously diagnosed glaucoma FIG. 7 a is a VEP trace array from left and right eyes. It shows normal amplitude signals throughout the field of the right eye, but reduced VEP amplitudes in parts of the left visual field. FIG. 7b(i) and (ii) show the corresponding subjective Humphrey visual field printouts from the right and left eyes respectively. Subjective losses of visual sensitivity are seen as gray areas on the upper right diagram and as black squares (representing high probability of abnormality compared to normals) on the total deviation and pattern deviation plots. The areas of defective vision seen in this subjective test are in the same area of the left visual field as they were in the objective VEP trace array. This confirms that the technique is capable of detecting visual defects in glaucoma.

Details of the recording method are as follows. The subject was comfortably seated in a chair and was asked to fixate on a red fixation cross at the center of the stimulus pattern seen in FIG. 1. The distance to the screen was 30 cm, corresponding to a total subtense of the stimulus of 52°. The subject was optimally refracted. Pupils were not dilated. Recording was collected using monocular stimulation. Data was recorded using a Grass amplifier Model 15 Neurodata (Astra-Med Inc, West Warwick, R.I.). The signal was amplified 100,000 times and band-pass filtered between 3 and 100 Hz. The data sampling rate was 300 Hz. Raw data was scanned in real time and segments contaminated by a high level of noise or eye movements were rejected.

The visual stimulus was generated on a computer screen with repetition rate 75 Hz. Luminance of the white check was 146 $cd/m^2$ and luminance of the black check 1.1 $cd/m^2$ producing a Michelson contrast of 99%. Background luminance of the screen was maintained at mean level of 73.5 $cd/m^2$. Four bipolar channels of different orientation were used. Two electrodes were positioned along the midline 2 cm above and 4 cm below the inion. Two additional electrodes were placed 4 cm on either side of the inion. Different combinations of the electrode connections produced four bipolar channels (as described by Klistorner and Graham): channel 1 (termed vertical or extended BOS)—upper and lower midline electrodes; channel 2 (horizontal)—two electrodes 4 cm on either side of the inion, channel 3 (right oblique)—electrode on the right side of the inion and lower midline electrode; channel 4 (left oblique)—electrode on the left side of the inion and lower midline electrode. Gold disc Grass electrodes (Astra-Med Inc, West. Warwick, R.I.) were used. Electrodes were mounted on a custom designed convex occipital-cross electrode holder. The lower midline electrode was negative for all vertical and oblique channels, while the left horizontal electrode was negative for the horizontal channel. One earlobe was connected with a clip electrode to serve as an earth.

Raw trace data was analysed using custom designed software. Peak-to-trough amplitudes for each wave within the interval of 50–165 msec were determined and compared between channels for every stimulated segment of the visual field. The wave of maximal amplitude from each point in the field was selected and a combined topographical map was created by the software. The combined trace array is shown in the FIGS. 4–6 and 7a, and represents the maximal signal obtained at each point of the field from any of the four channels.

The Humphrey visual field shows loss of subjective responses in the left eye superiorly and inferiorly on the nasal side. The multifocal VEP responses show loss of objective (electrophysiological) signal in the same area of the same eye. This confirms that the VEP signal accurately reflect loss of visual function. The right eye is normal on both techniques.

Figure 9:
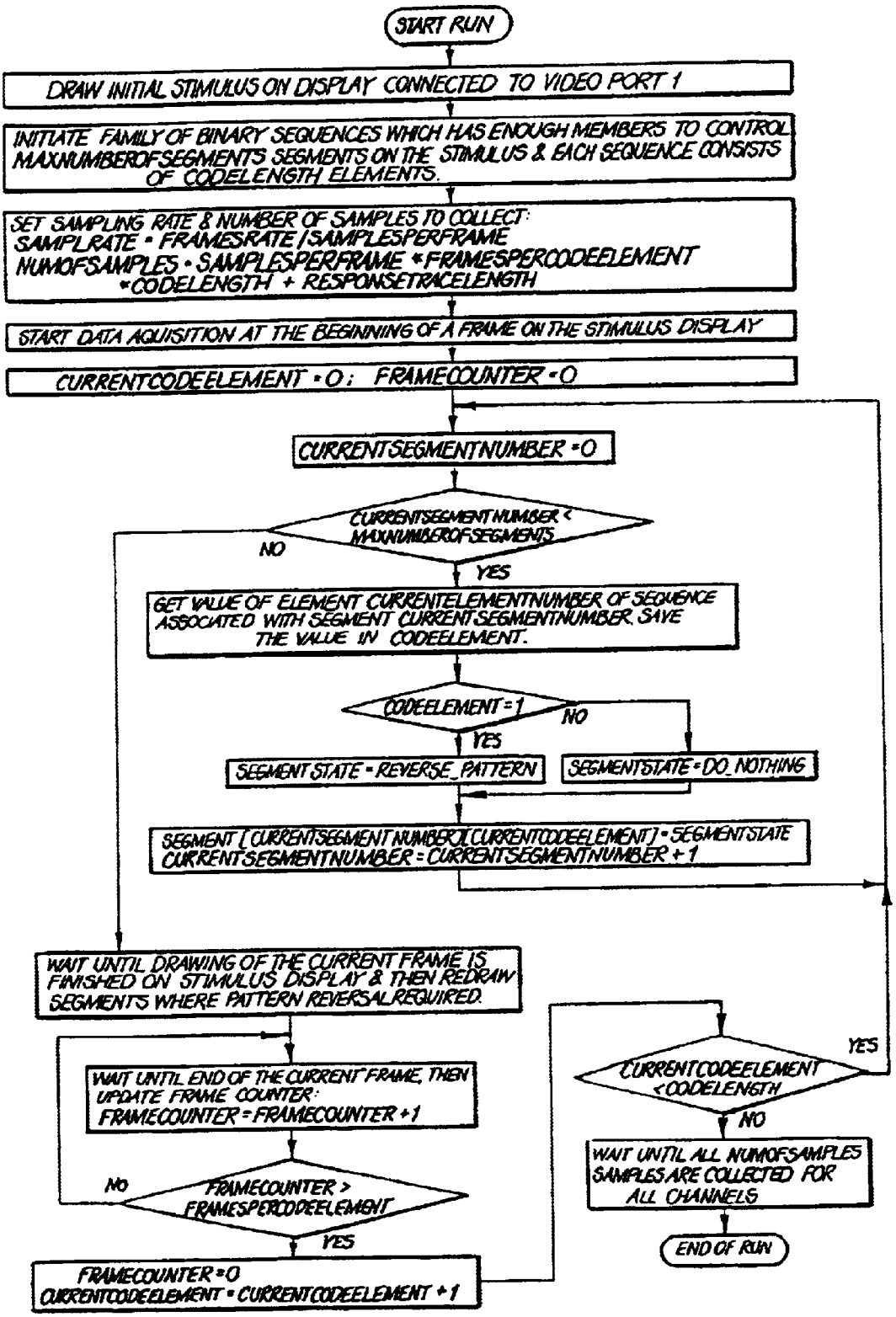
FIG. 9 is a flow diagram of a program for recording the measured responses using the first method of modulation described in text below.

FIG. 9 shows a data flow diagram of a program for recording the measured responses using the first method of modulation described in text above.

Figure 10:
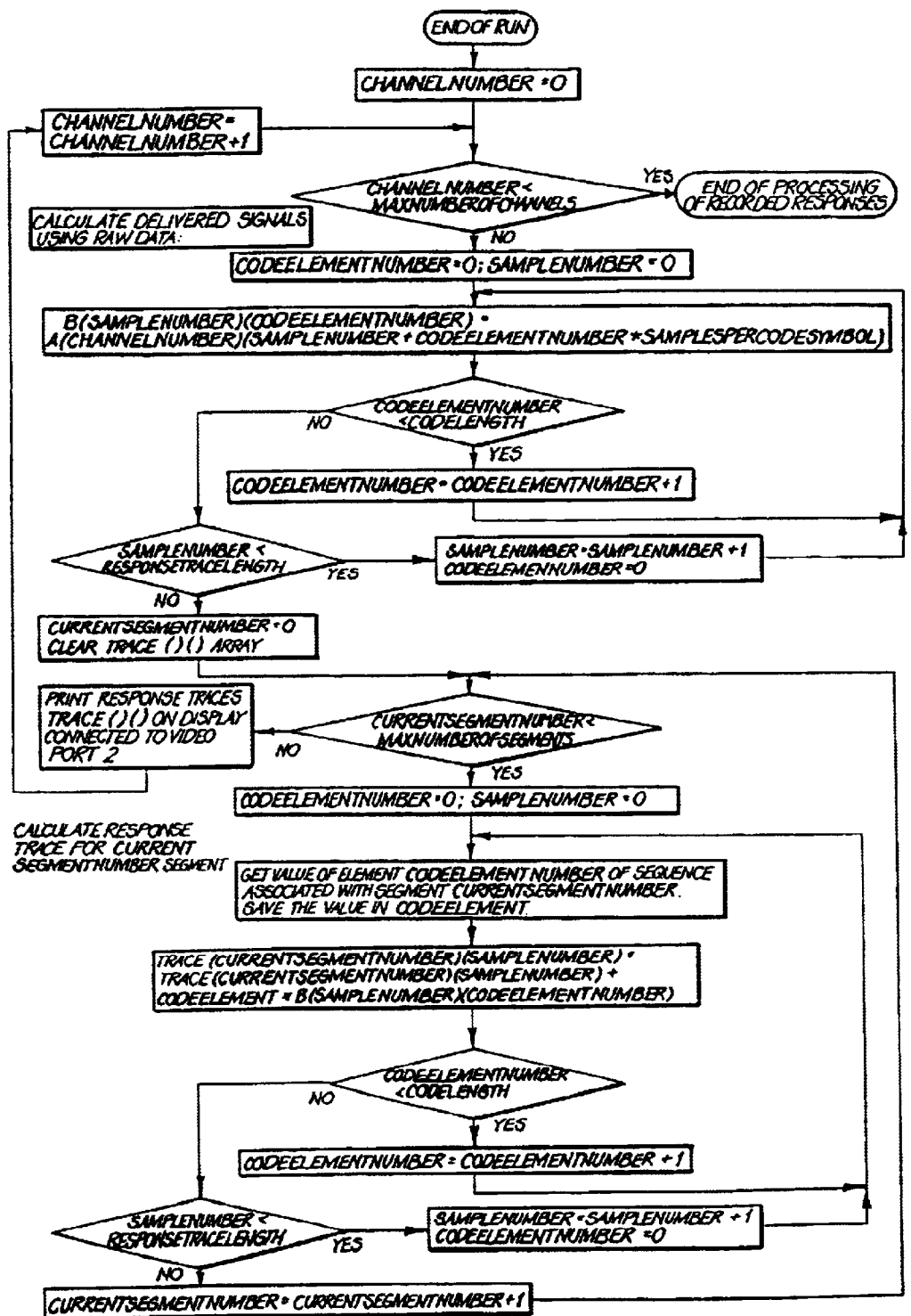
FIG. 10 is a flow diagram of a program for processing the recorded responses using the first method of modulation described in text below.

FIG. 10 is a data flow diagram of a program for processing the recorded responses using the first method of modulation described in text above. In the upper part of the diagram derived signals are calculated. Response traces are determined by cross-correlation between raw signals and the individual sequence from a family presented to each individual segment.

Industrial Applicability

The method and system of this invention will find wide use in-the medical field, specifically in the field of ophthalmology.

The foregoing describes only some embodiments of the invention and modifications can be made thereto without departing from the scope of the invention.

What is claimed is:

1. A method of providing a visual reaction map of at least part of the visual field of an eye of a subject, the method comprising:

(a) presenting to said visual field a plurality of segments each of the segments comprising an individually activated image;

(b) changing each of said individually activated images in each of said segments according to a binary sequence each of said images being changed in a different way from all other of said images whereby the changing of one of said images does not substantially correlate with the changing of any of the other of said images;

(c) detecting measurement signals in said subject while said visual field is presented with said changing;

(d) correlating said measurement signals with each of the binary sequences used to activate each of said individual segments; and (e) providing said visual reaction map from said correlating.

2. The method according to claim 1 further comprising:

(d)(i) repeating steps (a) to (d) at least once, and (d)(ii) progressively averaging said correlated measurement signals after each of said repeating steps of d(i).

3. The method according to claim 2 wherein steps (a) to (d) are repeated 4 to 10 times.

4. The method according to claim 2 wherein steps (a) to (d) comprise a run and wherein a different binary sequence member controls the same said image in each different run of a recording series to reduce the correlation between said images.

5. The method according to claim 1 further, comprising:

(f) determining from said visual reaction map whether said eye has one or more areas of defective vision.

6. The method according to claim 1 wherein the individually activated images are computer generated.

7. The method according to claim 6 wherein the sequences are selected from the group consisting of Gold and Kasami.

8. The method according to claim 1 wherein the property of the binary sequences which is responsible for substantial lack of correlation between said images is a level of cross-correlation of less than about 6% of the auto-correlation peak for a sequence of length 1023 samples or more.

9. The method according to claim 8 wherein the binary sequences are selected from the group consisting of Gold, Kasami, Bent and a combined family of Kasami and Bent.

10. The method according to claim 1 wherein each segment of said image is (a) a black and white pattern; (b) a colour pattern; or (c) a mixture of a (i) black and white and (ii) a colour pattern.

11. The method according to claim 10 wherein the sequences produce a pattern reversal.

12. The method according to claim 1 wherein said image in each segment is a diffuse white illumination and said sequences produce a change in brightness.

13. The method of claim 1 where said image in each segment is a diffuse colour illumination and said sequences produce a change in colour.

14. The method according to claim 1 wherein the measurement signals are detected by means of electrodes which are placed on the head or eyelids of the subject.

15. A method for assessing extent of visual field loss in a patient suffering from a neuro-opthalmic disorder, comprising producing a visual reaction map in accordance with the method of claim 1 and assessing the extent of visual field loss from said visual reaction map.

16. The method according to claim 15 wherein the neuro-opthalmic disorder is glaucoma.

17. A system for providing a visual reaction map a visual reaction map of at least part of the visual field of an eye of a subject, the system comprising:

(a) means for presenting to said visual field a plurality of segments each of the segments comprising an individually activated image;

(b) means for changing each of said individually activated images in each of said segments according to a binary sequence each of said images being changed in a different way from all other of said images whereby the changing of one of said images does not substantially correlate with the changing of any of the other of said images;

(c) means for detecting measurement signals in said subject while the visual field of the eye of said subject is presented with individually activated images in each of said segments which are changed according to a binary sequence each of said images being changed in a different way from all other of said images whereby the changing of one of said images does not substantially correlate with the changing of any of the other of said images;

(d) means for correlating said measurement signals with each of the binary sequences used to activate each of said images in said segments; and (e) means for providing said visual reaction map from said correlating.

18. The system according to claim 17 wherein the individually activated images are computer generated.

19. The system according to claim 18 wherein the means for presenting said visual field comprises a computer display or any other means of visualization of computer generated images.

20. The system according to claim 17 and wherein the means for changing the individually activated images comprises a computer program to effect said changes.

21. The system according to claim 17 wherein the means for detecting measurement signals comprises electrodes placed on the head or on the eyelids of the said subject, wherein the placement is effective for detecting said signals.

22. The system according to claim 21 wherein when the electrodes are placed on the head, said electrodes are placed as follows one electrode is placed along the midline above the inion; one electrode is placed along the midline below the inion; and two electrodes are placed on either side of the inion.

23. The system according to claim 22 wherein one electrode is placed along the midline about 2 cm above the inion; one electrode is placed along the midline about 4 cm below the inion; and two electrodes are placed about 4 cm on either side of the inion.

24. The system according to claim 17 wherein the means for correlating said measurement signals comprises a computer programmed to correlate the individually activated images and the measurement signals.

* * * * *